United States Patent [19]

D'Silva

[11] Patent Number: 4,486,447

[45] Date of Patent: Dec. 4, 1984

[54] PESTICIDAL SYMMETRICAL BIS-SULFENYLATED-BIS CARBAMATE COMPOUNDS

[75] Inventor: Themistocles D. J. D'Silva, South Charleston, W. Va.

[73] Assignee: Union Carbide Corporation, Danbury, Conn.

[21] Appl. No.: 507,468

[22] Filed: Jun. 24, 1983

Related U.S. Application Data

[62] Division of Ser. No. 903,533, May 8, 1978, Pat. No. 4,400,389.

[51] Int. Cl.$^3$ ............... C07C 125/06; C07C 121/50; C07C 121/60; C07C 121/74; C07C 125/04; A01N 43/08; A01N 47/10

[52] U.S. Cl. .................. 424/285; 260/465 D; 424/275; 424/276; 424/277; 424/278; 424/282; 424/300; 424/304; 549/15; 549/19; 549/21; 549/22; 549/37; 549/65; 549/365; 549/366; 549/467; 560/10; 560/16; 560/24; 560/27; 560/29; 560/31; 560/133; 560/134; 560/135; 560/136; 560/137; 560/158

[58] Field of Search ............... 424/285, 275, 276, 277, 424/278, 282, 300, 304; 260/465 D; 549/15, 19, 21, 22, 37, 65, 365, 366, 467; 560/10, 16, 24, 27, 29, 31, 133, 134, 135, 136, 137, 158

[56] References Cited

U.S. PATENT DOCUMENTS

| | | | |
|---|---|---|---|
| 3,450,818 | 6/1969 | Pianka et al. | 424/300 |
| 3,679,733 | 2/1972 | Brown | 560/137 |
| 3,817,944 | 6/1974 | Jones | 560/25 |
| 3,950,534 | 4/1976 | Yaghihara et al. | 424/300 |
| 4,004,031 | 1/1977 | Drabek | 424/327 |
| 4,032,654 | 6/1977 | Corty | 424/300 |
| 4,044,045 | 8/1977 | Perkow et al. | 424/300 |
| 4,078,015 | 3/1978 | Leitheiser et al. | 560/25 |
| 4,122,204 | 10/1978 | D'Silva | 260/346.73 |

FOREIGN PATENT DOCUMENTS

| | | | |
|---|---|---|---|
| 1081460 | 12/1960 | Fed. Rep. of Germany | 260/479 C |
| 605067 | 5/1960 | Italy | 560/137 |

Primary Examiner—Douglas W. Robinson
Attorney, Agent, or Firm—Clement J. Vicari

[57] ABSTRACT

Bis-sulfenylated bis-carbamate compounds exhibit activity against insect and mite pests.

9 Claims, No Drawings

PESTICIDAL SYMMETRICAL BIS-SULFENYLATED-BIS CARBAMATE COMPOUNDS

This application is a division of our prior U.S. application Ser. No. 903,533 filed May 8, 1978 which is now U.S. Pat. No. 4,400,389.

This invention relates to symmetrical bis-sulfenylated bis-carbamate compounds and methods of preparing same. This invention is also directed to insecticidal, nematocidal and miticidal compositions comprising an acceptable carrier and an nematocidally, insecticidally or miticidally effective amount of a compound of this invention and to a method of controlling nematodes, insects and mites which comprises subjecting them to an insecticidally, miticidally or nematocidally effective amount of a compound of this invention.

More particularly, this invention relates to compounds of the formula:

wherein:

X is:

A. a substituted or unsubstituted divalent alkylene, alkenylene, alkynylene, monocyclic arylene, bicyclic arylene, biphenylene or a divalent alkylene chain which includes one oxygen, sulfur, sulfinyl, sulfonyl or nitrogen, wherein the permissible substituents are one or more alkyl, fluoro, nitro, chloro or, bromo groups or B. A divalent organic radical of the formula:

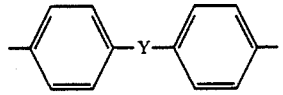

wherein:

Y is oxygen, sulfur, sulfinyl, sulfonyl, alkylene, haloalkylene, alkenylene or haloalkenylene;

$R_1$ is alkyl having from one to four carbon atoms;

$R_2$ is:

A. dihydrobenzofuranyl, naphthyl, tetrahydronaphthyl, benzothienyl, indanyl, benzodioxalanyl, benzofuranyl or benzodioxanyl groups, all of which may be either unsubstituted or substituted with one or more alkyl groups; or B. phenyl, either unsubstituted or substituted with one or more halo, cyano, nitro, cycloalkyl, alkyl, alkylthio, alkylsulfinyl 2-dithiolanyl, alkylsulfonyl, alkylthioalkyl, alkylsulfinylalkyl, 2-dioxalanyl,alkylsulfonylalkyl, amino,alkylamino, dialkylamino, alkynyloxy, alkoxycarbonylamino, trihalomethyl, N,N-dialkylformamidino, or alkoxy; or

C.

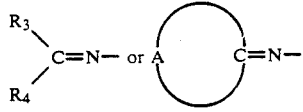

wherein $R_3$ is hydrogen,alkyl, alkylthio alkylsulfinyl, alkylsulfonyl, aminocarbonyl, alkylaminocarbonyl, dialkylaminocarbonyl or cyano;

$R_4$ is alkyl, alkylthio, alkylsulfinyl, alkylsulfonyl, aminocarbonyl, alkylaminocarbonyl,dialkylaminocarbonyl or alkanoyl, all of which may be unsubstituted or, except for aminocarbonyl, substituted with one or more cyano, amido, nitro, alkylthio, alkylsulfonyl or alkylsulfinyl;

A is a divalent alkylene chain having from 2 to 24 aliphatic carbon atoms completing a five or six membered ring structure which includes one, two or three groups selected from the group consisting of divalent oxygen, sulfur, sulfinyl, sulfonyl, amino, alkylamino, alkylimino or carbonyl groups;

The following miticidally and insecticidally active compounds are illustrative of the compounds of this invention all of which can be conveniently prepared by the process of this invention simply by selecting appropriate starting materials for use in the procedures described below:

1,2-Bis-[[N-methyl-N-[N'-(1-ethylthioethylideneiminooxycarbonyl N-methylaminosulfenyl]carbamoyloxy]ethane.

2,2'-Bis-[[N-methyl-N-[N'-(1-isopropylthioethylideneiminooxycarbonyl)-N'-methylaminosulfenyl]carbamoyloxy]]diethyl ether 1,6-Bis-[[N-methyl-N-[N'-(1-butylthioethylideneiminooxycarbonyl)-N'-methylaminosulfenyl]carbamoyloxy]]hexane.

4,4'-Bis-[[N-methyl-N-[N'-(2-methyl-2-methylthiopropylideneiminooxycarbonyl)-N'-methylaminosulfenyl]carbamoyloxy]]biphenyl 4,4'-Bis-[[N-methyl-N-[N'-(2-methyl-2-methylsulfonylpropylideneiminooxycarbonyl)-N'-methylaminosulfenyl]carbamoyloxy]]diphenyl sulfide.

1,2-Bis-[[N-methyl-N-[N'-(2-methyl-2-methylsulfonylpropylideneiminooxycarbonyl)-N'-methylaminosulfenyl]carbamoyloxy]]benzene 1,2-Bis-[[N-methyl-N-[N'-(1,3-dithiane-2-ylideneiminooxycarbonyl)-N'-methylaminosulfenyl]-carbamoyloxy]]

1,2-Bis-[[N-methyl-N-[N'-(1,3-dithiolane-2-ylideneiminooxycarbonyl)-N'-methylaminosulfenyl]-carbamoyloxy]]ethane.

2,2'-Bis-[[N-methyl-N-[N'-(thiophane-2-ylideneiminooxycarbonyl)-N'-methylaminosulfenyl]-carbamoyloxy]]diethyl ether.

1,6-Bis[[N-methyl-N-[N'-(thiophane-3-ylideneimioxycarbonyl)-N'-methylaminosulfenyl]carbamoyloxy]]-hexane.

1,4-Bis-[[N-methyl-N-[N'-(3,3-dimethyl-1,4-dioxane-2-ylideneiminooxycarbonyl)-N'-methylaminosulfenyl]-carbamoyloxy]]2-butene.

1,2-Bis-[[N-methyl-N-[N'-(4-methyl-1,4-thiazine-3-one-2-ylideneiminooxycarbonyl)-N'-methylaminosulfenyl]carbamoyloxy]ethane.

1,2-Bis-[[N-methyl-N-[N'-(4-methyl-1,4-oxazine-3-one-2-ylideneiminooxycarbonyl)-N'-methylaminosulfenyl]carbamoyloxy]]ethane.

1,2-Bis-[[N-methyl-N-[N'-(3,3-dimethyl-1,4-thiazine-5-one-2-ylideneiminooxycarbonyl)-N'-methylaminosulfenyl]carbamoyloxy]]ethane.

1,2-Bis-[[N-methyl-N-[N'-(1,3,5-trithiane-2-ylideneiminooxycarbonyl)-N'-methylaminosulfenyl]-carbamoyloxy]]ethane 1,2-Bis-[[N-methyl-N-[N'-(1,3,5-oxadithiane-4-ylideneiminooxycarbonyl)-N'-methylaminosulfenyl]carbamoyloxy]]ethane 2,2'-Bis-[[N-methyl-N-[N'-(2-methylimino,5,5-dimethyl-4-ylideneiminooxycarbonyl)-N'-methylaminosulfenyl]carbamoyloxy]diethyl]]ether.

2,2'-Bis-[[N-methyl-N-[N'-(1,4-oxathiane-2-ylideneiminooxycarbonyl)-N'-methylaminosulfenyl]carbamoyloxy]diethyl sulfide 2,2'-Bis-[[N-methyl-N-[N'-(4,5,5-trimethyl-thiazolidin-3-one-2-ylideneiminooxycarbonyl)-N'-methylaminosulfenyl]carbamoyloxy]]diethyl sulfide.

1,2-Bis-[[N-methyl-N-[N'-(3,5,5-trimethyl-thiazolidin-4-one-2-ylideneiminooxycarbonyl)-N'-methylaminosulfenyl]carbamoyloxy]]ethane.

1,2-Bis-[[N-butyl-N-[N'-(1-methylthioethylideneiminooxycarbonyl)-N'-butylaminosulfenyl]carbamoyloxy]]ethane.

1,2-Bis-[[N-methyl-N-[N'-(3,3-dimethyl-1-methylthio-2-butylidene iminooxycarbonyl)-N'-methylaminosulfenyl]carbamoyloxy]]ethane 2,2-Diphenyl-4,4'-bis-[[N-butyl-N-[N'-(1,4-dithiane-4-oxide-2-ylideneiminooxycarbonyl)-N'-butylaminosulfenyl]carbamoyloxy]]propane 2,2'-Bis-[[N-methyl-N-[N'-(5,5-dimethyl-1,3-dithiolane-4-ylideneiminooxycarbonyl)-N'-methylaminosulfenyl]carbamoyloxy]]diethylsulfone 2,2'-Bis-[[N-methyl-N-[N'-(5-methyl-1,3-oxathiolane-4-ylideneiminooxycarbonyl)-N'-methylaminosulfenyl]carbamoyloxy]]diethyl ether.

1,2-Bis-[[N-methyl-N-[N'-(3,5-diisopropylphenyloxycarbonyl)-N'-methylaminosulfenyl]carbamoyloxy]]ethane .

1,6-Bis[[N-methyl-N-[N'-(2-isopropoxyphenyloxycarbonyl-N'-methylaminosulfenyl]carbamoyloxy]]hexane 2,2'-Bis-[[N-methyl-N-[N'-(3,5-dimethyl-4-methylthiophenyloxycarbonyl)-N'-methylaminosulfenyl]carbamoyloxy]]diethyl ether 1,2-Bis-[[N-methyl-N-[N'-(1-naphthyloxycarbonyl)-N'-methylaminosulfenyl]carbamoyloxy]]ethane.

1,2-Bis-[[N-methyl-N-[N'-4-(2,2-dimethylbenzodioxanyloxycarbonyl)-N'-methylaminosulfenyl]carbamoyloxy]]ethane.

2,2'-Bis-[[N-methyl-N-[N'-(3,5-dimethyl-4-dimethylaminophenyloxycarbonyl)-N'-methylaminosulfenyl]carbamoyloxy]]diethyl ether 1,2-Bis-[[N-methyl-N-[N'-(3-isopropyl-4-dimethylaminomethyleneiminophenyloxycarbonyl)-N'-methylaminosulfenyl]carbamoyloxy]]ethane, dihydrochloride.

4,4'-Bis-[[N-methyl-N-[N'-(2-ethylthiomethylphenyloxycarbonyl)-N'-methylaminosulfenyl]carbamoyloxy]]diphenyl ether 4,4'-Bis-[[N-methyl-N-[N'-(2-chlorophenyloxycarbonyl)-N'-methylaminosulfenyl]carbamoyloxy]]diphenyl sulfide 1,4-Bis-[[N-methyl-N-[N'-7-(2,3-dihydro-2-methylbenzofuranoxycarbonyl)-N'-methylaminosulfenyl]carbamoyloxy]]-2-butyne 1,4-Bis-[[N-methyl-N-(2-propynyloxyphenyloxycarbonyl)-N'-methylaminosulfenyl]carbamoyloxy]]-2-butene.

1,2-Bis-[[N-methyl-N-[N'-(1-(2-cyanoethylthio)ethylideneiminooxycarbonyl)-N'-methylaminosulfenyl]carbamoyloxy]]ethane 1,2-Bis-[[N-methyl-N-[N'-(2-cyano-2-methylpropylideneiminooxycarbonyl)-N'-methylaminosulfenyl]carbamoyloxy]]benzene 1,2-Bis-[[N-methyl-N-[N'-(2-methyl-2-nitropropylideneiminooxycarbonyl)-N'-methylaminosulfenyl]carbamoyloxy]ethane 1,2-Bis-[[N-methyl-N-[N'-(3,3-dimethyl-1-methylsulfinyl-2-butylideneiminooxycarbonyl)-N'-methylaminosulfenyl]carbamoyloxy]ethane 1,2-Bis-[[N-methyl-N-[N'-(1-dimethylaminocarbonyl-1-methylthiomethylideneiminooxycarbonyl)-N'-methylaminosulfenyl]carbamoyloxy]]ethane.

Many of the compounds of this invention exhibit insecticidal, miticidal and nematocidal activity to a lesser or greater extent. Accordingly, these compounds are useful for the control of insect, nematode and mite pests. Some of these compounds exhibit very high levels of miticidal, insecticidal and nematocidal activity in extremely small dosages while others require larger dosages to be effective.

In general, the compounds of this invention are either totally lacking in phytotoxicity or exhibited only minimal phytotoxicity with respect to the economically important crop species tested. These compounds also exhibit substantially reduced levels of mammalian toxicity as compared to known pesticidal compounds having a comparable spectrum of activity against insect and mite pests.

Preferred because of their higher levels of insecticidal, miticidal and nematocidal activity and because of their utility as intermediates in the preparation of other pesticidally active compounds are the compounds of this invention in which $R_1$ is methyl;

$R_2$ is:

(a) naphthyl, phenyl,dihydrobenzofuranyl or dihydrobenzofuranyl substituted with one or more alkyl, 5,6,7,8-tetrahydronaphthyl, or phenyl substituted with one or more alkyl, dialkylamino, alkynyloxy, alkoxy or alkylthio;

(b)

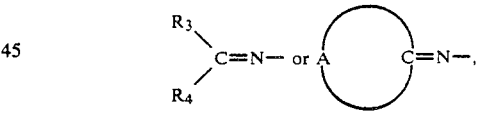

wherein:

$R_3$ is hydrogen, alkyl, alkylthio or cyano;

$R_4$ is alkyl, nitroalkyl, alkylthio, alkylsulfinyl, alkylsulfonyl, alkylthioalkyl, alkylsulfinylalkyl, alkylsulfonylalkyl, alkanoyl, cyanoalkylthio or dialkylaminocarbonyl;

A is a divalent alkylene chain having from 2 to 24 aliphatic carbon atoms completing a 2-oximino-1,4 dithiane, 2-oximino-1,3-dithiane, 4-oximino-1,3-dithiolane, 2-oximino-1,4-dioxane, 2-oximino-1,4-oxathiane, 2-oximino tetrahydro-1,4-thiazine-3-one, 2-oximino-1,3-dithiolane, 2-imino-4-oximino-1,3-dithiolane, 3-oximinothiophene, 2-oximinothiophane, 2-oximino-tetrahydro-1,4-oxazin-3-one, 2-oximino-1,3,5-trithiane, 4-oximino-1,3,5-oxadithiane, 2-oximino-1,3-thiazolidin-4-one, 5-oximino-1,3-thiazolidin-4-one or 2-oximino-tetrahydro-1,4-thiazine-5-one ring structure, wherein sulfur may be in any of its oxidation states.

The bis-sulfenylated-bis-carbamate compounds of this invention can be prepared by a variety of methods.

One preferred method is illustrated by the reaction scheme set forth below in which $R_1$, $R_2$ and X are as described above:

METHOD I

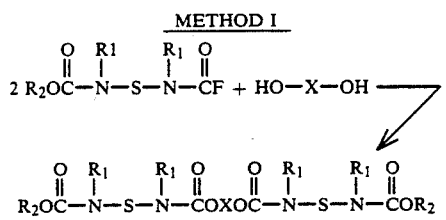

$$2\ R_2OC(O)-N(R_1)-S-N(R_1)-CF(O) + HO-X-OH \longrightarrow$$

$$R_2OC(O)-N(R_1)-S-N(R_1)-C(O)OXOC(O)-N(R_1)-S-N(R_1)-C(O)R_2$$

In the procedure illustrated in METHOD I, one equivalent of the dihydroxy reactant is reacted with two equivalents of the intermediate carbamate carbamoyl fluoride reactant in an appropriate solvent in the presence of at least two equivalents of an acid acceptor. Normally, an aprotic organic solvent is employed as the reaction solvent. Illustrative of useful reaction solvents are saturated and unsaturated aliphatic and aromatic hydrocarbons, e.g. hexane, cyclohexane, octane, dodecane naphtha, decalin, kerosene, tetrahydronapthalene, cycloheptane, alkylcycloalkane, benzene, toluene, xylene, naphthalene, alkylnapthalene, or the like; ethers such as tetrahydrofuran, tetrahydropyran, diethyl ether, dioxane, 1,2-dimethoxybenzene, 1,2-ethoxybenzene, the mono and dialkyl ethers of ehtylene glycol, of dipropylene glycol, of butylene glycol, of diethylene glycol, of dipropylene glycol, or chlorinated aliphatic hydrocarbons as for example, chloroform, dichloromethane, methylene dichloride, 1,1-dichloroethane, carbon tetrachloride or the like.

The acid acceptor utilized in the conduct of the reaction of METHOD I may be either an organic or an inorganic base. Useful inorganic bases include alkali metal hydroxides, alkaline earth metal hydroxides and the like. Illustrative of useful organic bases are tertiary amines, alkali metal alkoxides and the like. Preferred acid acceptors are tertiary amines such as triethylamine, pyridine or trimethylamine.

The intermediate carbamate carbamoyl halide reactant can be conveniently prepared by reacting one equivalent of an oxime or hydroxyl reactant with one equivalent of a bis-(N-alkyl-N-fluorocarbonyl)amino sulfide reactant in the presence of one equivalent of an acid acceptor, preferably in an inert solvent. The bis-(N-alkyl-N-fluorocarbonylamino)sulfide reactant, in turn, can be conveniently prepared by reacting sulfur dichloride with N-alkylcarbamoyl fluoride in an aprotic solvent such as toluene in the presence of an acid acceptor as for example triethylamine or pyridine. This procedure is described in more detail in the U.S. Pat. No. 3,639,471.

Di-hydroxylated compounds employed as reactants in the reaction of METHOD 1 as well as oxime and hydroxyl precursors used in the preparation of the intermediate carbamate carbamoyl halide compound are well known compounds that can be prepared by well known synthetic procedures or obtained from commercial sources.

The following specific examples are presented to particularly illustrate the invention:

EXAMPLE I

Preparation of S-Methyl-N-[N'-(N''-methyl-N''-fluorocarbonylaminosulfenyl)-N'-methylcarbamoyloxy]thioacetimidate To a solution of 0.714 g of S-methyl-N-hydroxyacetimidat and 1.36 g of N,N'-bis-(N-methyl-N-fluorocarbonylamino)sulfide in 15 ml of dioxane was added dropwise with stirring 0.687 g of triethylamine. After the solution was allowed to stand for 20 hrs., it was diluted with water and extracted with ethyl acetate. The organic extract was washed with water, dried over magnesium sulfate and concentrated under reduced pressure to afford 1.0 g of the product. The material was crystallized from isopropylether-ethyl acetate solution, m.p. 102°–104° C.

Calc'd for $C_7H_{12}FN_3O_3S_2$: C, 36.35; H, 5.42; N, 14.13; Found: C, 36.60; H, 5.57; N, 13.39.

EXAMPLE II

Preparation of 2-Methyl-2-methylthiopropionaldehdye 0-[N-methyl-N-(N'-methyl-N'-fluorocarbonylaminosulfenyl)carbamoyl]oxime To a solution of 8.63 g of N,N'-bis-(N-methyl-N-fluorocarbonylamino)sulfide and 6.66 g of 2-methyl-2-methylthiopropionaldoxime in 40 ml of dioxane and 40 ml of toluene, was added dropwise at 0°–5° C. with stirring, 5.06 g of triethylamine over a period of one hour. The reaction mixture was allowed to stand overnight. It was diluted with water and extracted in ethyl acetate. The organic extract was washed with water, was dried over magnesium sulfate and concentrated to afford 2.8 g of a residual oil which crystallized on standing. m.p. 70°–71° C.

Calc'd for $C_9H_{16}FN_3O_3S_2$: C, 36.35; H, 5.42; N, 14.13; Found: C, 36.60; H, 5.57; N, 13.39.

EXAMPLE III

Preparation of 2,3-Dihydro-2,2-dimethyl-7-[N-methyl-N-(N'-methyl-N'-fluorocarbonylaminosulfenyl)carbamoyloxy]benzofuran To a solution of 5.0 g of N,N'-bis-(N-methyl-N-fluorocarbonylamino)sulfide and 5.0 g of 2,3-dihydro-2,2-dimethylbenzofuran-7-ol in 75 ml of dioxane was added 4.0 g of triethylamine. After allowing the reaction mixture to stand at ambient temperature for 6 days, it was diluted with 200 ml of water and was extracted in ethyl acetate. The organic extract was washed with water, dried over magnesium sulfate and concentrated. Purification by chromatography using silica gel afforded 5.0 g of the product as a viscous oil.

Calc'd for $C_{14}H_{17}FN_2O_4S$: C, 51.21; H, 5.21; N, 8.53; Found: C, 51.90; H, 5.34; N, 8.60.

EXAMPLE IV

Preparation of 2-[[O-[N-methyl-N-methyl-N-(N'-methyl-N'-fluorocarbonylaminosulfenyl)carbamoyl]oximino]]-1,4-dithiane To a suspension of 3.68 g of N,N'-bis-(N-methyl-N-fluorocarbonylamino)sulfide and 2.98 g of 2-oximino-1,4-dithiane in 125 ml of toluene was added with stirring 2.02 g of triethylamin. On completion of the addition of the amine all the material was in solution. The reaction mixture was stirred at ambient temperature for 20 hours. The insoluble bis-carbamate (1.0 g) was removed by filtration. The filtrate was washed with water, dried over magnesium sulfate and concentrated under reduced pressure to afford 3.6 g of a solid product. Recrystallized from isopropyl alcohol m.p. 124°–126° C.

Calc'd for $C_8H_{12}FN_3O_3S_3$: C, 30.66; H, 3.86; N, 13.41; Found: C, 30.71; H, 3.75; N, 13.17.

EXAMPLE V

Preparation of 1,2-Bis-[[N-methyl-N-[N'-(1-methylthioethylideneiminooxycarbonyl) N'-methylaminosulfenyl]carbamoyloxy]]benzene.

To a solution of 0.82 g (0.0075 m) of catechol and 3.56 g (0.015 m) of S-methyl-N-[N'-(N''-methyl-N''-fluorocarbonylaminosulfenyl)-N'-methylcarbamoyloxy]thioacetimidate (prepared according to the procedure described in Example I), in 50 ml of toluene was added 1.51 g (0.015 m) of triethylamine. After stirring for hours, 10 ml. of methylene chloride was added and continued stirring for an additional period of 24 hours. The solid was filtered and recrystallized from ethyl acetate to afford 0.8 g of the product. m.p. 152°–154° C. An additional 0.7 g was isolated from the mother liquor after chromatographic purification.

Calc'd for $C_{20}H_{28}N_6O_8S_4$: C, 39.46; H, 4.64; N, 13.81; Found: C, 39.38; H, 4.65; N, 13.53.

EXAMPLE VI

Preparation of-1,3-Bis-[[N-methyl-N-[N'-(1-methylthioethylideneiminooxycarbonyl)N'-methylaminosulfenyl]-carbamoyloxy]]benzene To a solution of 1.65 g (0.015 m) of resorcinol and 7.12 g (0.03 m) of S-methyl-N-[N'-(N''-methyl-N''-fluorocarbonylaminosulfenyl)N'-methylcarbamoyloxy]thioacetimidate in 100 ml of methylene chloride was added 3.06 g (0.03 m) of triethylamine. The reaction mixture was heated under reflux for 13 hours and stirred at ambient temperature for 88 hours. Washed with dilute sodium hydroxide solution followed by water wash and dried over magnesium sulfate and concentrated under reduced pressure. Purification through a dry silica gel column afforded 1.2 g of the product m.p. 155°–165° C.

Calc'd for $C_{20}H_{28}N_6O_8S_4$: C, 39.46; H, 4.63; N, 13.81; Found: C, 40.65; H, 5.23; N, 12.81.

IR and NMR spectra supported the molecular structure.

EXAMPLE VII

Preparation of 1,2-Bis-[[N-methyl-N-[N'-(1-methylthioethylideneiminooxycarbonyl)N'-methylaminosulfenyl]-carbamoyloxy]]ethane To a solution of 1.24 g (0.02 m) of ethylene glycol and 10.77 g (0.04 m) of S-methyl-N-[N'-(N''-methyl-N''-fluorocarbonylaminosulfenyl)N'-methylcarbamoyloxy]thioacetimidate in 100 ml of toluene warmed to 35° C. was added with stirring 4.05 g (0.04 m) of triethylamine. The mixture was heated at 50° C. for 3 hours and after stirring at room temperature overnight was heated again between 50°–60° C. for an additional period of 24 hours. While still hot the solid precipitate was removed by filtration. The solid was taken in methylene chloride, was washed with water, dried over magnesium sulfate and concentrated to a residual solid. Crystallization from methylene chloride afforded 5.55 g of a white solid. m.p. 177°–180° C.

Calc'd for $C_{16}H_{28}N_6O_8S_4$: C, 34.27; H, 5.03; N, 14.99; Found: C, 33.73; H, 5.04; N, 14.20.

EXAMPLE VIII

Preparation of 2,2'-Bis-[[N-methyl-N-[N'-(1,4-dithiane-2-ylideneiminooxycarbonyl)N'-methylaminosulfenyl]carbamoyloxy]]diethyl ether.

To a suspension of 1.70 g (0.016 m ) of diethylene glycol, 10.0 g (0.032 m) of 2-[[0-[N-methyl-N-(N'-methyl-N'-fluorocarbonylaminosulfenyl)carbamoyl]-oximino]]-1,4-dithiane (prepared according to the procedure described in Example IV) in 150 ml of dioxane was added 3.23 g (0.032 m) of triethylamine. The reaction mixture was heated at 50° C. for 16 hours and at 70° C. for 6 days. On cooling the mixture was diluted with water and extracted in ethyl acetate. The organic extract was washed with dilute sodium hydroxide solution and water until neutral. It was dried over magnesium sulfate and concentrated to afford 8.2 g of an amorphous solid. Crystallized from ethyl acetateisopropyl ether. m.p. 123°–126° C.

Calc'd for $C_{20}H_{32}N_6O_9S_6$: C, 34.67; H, 4.66; N, 12.13; Found: C, 35.53; H, 4.79; N, 11.55.

EXAMPLE IX

Preparation of 1,2-Bis-[[N-methyl-N-[N'-(2-methyl-2-methylthiopropylideneiminooxycarbonyl)-N'-methylaminosulfenyl]carbamoyloxy]ethane To a solution of 7.43 g (0.025 m) of 2-methyl-2-methylthiopropionaldehyde 0-[N-methyl-N-(N'-methyl-N'-fluorocarbonylaminosulfenyl)carbamoyl]oxime (prepared according to the procedure described in Example II) in 60 ml of toluene was added 0.77 g (0.0125 m) of ethylene glycol dissolved in 2 ml of dioxane followed by the slow addition of 2.53 g (0.025 m) of triethylamine. The slight exotherm raised the temperature of the reaction mixture from 27° C. to 30.5° C. After stirring at ambient temperature for 16 hours, the reaction mixture was diluted with 100 ml of toluene and was washed with water. The toluene solution was dried over magnesium sulfate and concentrated to afford 7.7 g of a colorless oil which crystallized on triturating and cooling. Crystallized from ethyl acetateisopropyl ether. m.p. 97°–99.5° C.

Calc'd for $C_{20}H_{36}N_6O_8S_4$: C, 38.94; H, 5.88; N, 13.63; Found: C, 38.84; H, 5.95; N, 13.41.

EXAMPLE X

Preparation of 1,2-Bis-[[N-methyl-N-[N'-7-(2,3-dihydro-2,2-dimethylbenzofuranyloxycarbonyl)-N'-methylaminosulfenyl]-carbamoyloxy]]ethane To a solution of 0.66 g (0.0107 m) of ethylene glycol and 7.0 g (0.0213 m) of 2,3-dihydro-2,2-dimethyl-7-[N-methyl-N-(N'-methyl-N'-fluorocarbonylaminosulfenyl)carbamoyloxy]benzofuran (prepared according to the procedure described in Example III), in 150 ml of dioxane was added dropwise with stirring 2.16 g (0.0213 m) of triethylamine. The reaction mixture was heated at 50°–75° C. for about 9 days. On cooling it was diluted with water and extracted in ethyl acetate. The organic extract was washed successively with water, dilute sodium hydroxide and water until neutral. It was dried over magnesium sulfate and concentrated to afford 5.7 g of a residual oil. The product was purified by low pressure column chromatographic technique using silica gel. m.p. 130°-132° C.

Calc'd for $C_{30}H_{38}N_4O_{10}S_2$: C, 53.08; H, 5.64; N, 8.25; Found: C, 52.87; H, 5.54; N, 8.09.

The compounds of Examples XI to XXIX were prepared by the method of Examples V to X by using appropriate starting materials. The physical properties of the compounds of Examples XI to XXIX are set forth in Table I below:

TABLE I
PHYSICAL PROPERTIES $$R_2OC(=O)-N(CH_3)-S-N(CH_3)-COXOC(=O)-N(CH_3)-S-N(CH_3)-COR_2$$

| Example | $R_2$ | X | MP °C. | Molecular Formula | Calculated C | Calculated H | Calculated N | Found C | Found H | Found N |
|---------|-------|---|--------|-------------------|---|---|---|---|---|---|
| XI | −N=C(CH₃)−SCH₃ | −C₆H₄− (para) | 195-196.5 | $C_{20}H_{28}N_6O_8S_4$ | 39.46 | 4.64 | 13.81 | 39.25 | 4.57 | 13.63 |
| XII | −N=C(CH₃)−SCH₃ | naphthylene (1,4) | 172-174 | $C_{24}H_{30}N_6O_8S_4$ | 43.75 | 4.59 | 12.76 | 43.73 | 4.61 | 12.52 |
| XIII | −N=C(CH₃)−SCH₃ | −C₆H₄−C(CH₃)₂−C₆H₄− | 149-151 | $C_{29}H_{38}N_6O_8S_4$ | 47.91 | 5.27 | 11.56 | 47.89 | 5.24 | 11.37 |
| XIV | −N=C(CH₃)−SCH₃ | −C₆H₄−S−C₆H₄− | 110-116 | $C_{26}H_{32}N_6O_8S_5$ | 43.56 | 4.50 | 11.72 | 43.57 | 4.50 | 11.43 |
| XV | −N=C(CH₃)−SCH₃ | −C₆H₄−SO₂−C₆H₄− | 155-162 | $C_{26}H_{32}N_6O_{10}S_5$ | 41.70 | 4.31 | 11.22 | 41.54 | 4.41 | 11.04 |
| XVI | −N=C(CH₃)−SCH₃ | −CH₂CH₂SO₂−CH₂−CH₂− | oil | $C_{18}H_{32}N_6O_{10}S_5$ | 33.12 | 4.94 | 12.88 | 32.51 | 4.97 | 11.67 |
| XVII | −N=C(CH₃)−SCH₃ | −(CH₂)₆− | 150-1525 | $C_{20}H_{36}N_6O_8S_4$ | 38.94 | 5.88 | 13.63 | 38.96 | 5.91 | 13.18 |
| XVIII | −N=C(CH₃)−SCH₃ | −C₆H₄−C(=CCl₂)−C₆H₄− | 217-219 | $C_{28}H_{32}Cl_2N_6O_8S_4$ | 43.12 | 4.14 | 10.78 | 42.89 | 3.99 | 10.81 |
| XIX | −N=C(CH₃)−SCH₃ | −(CH₂)₂−O−(CH₂)₂− | 76-79 | $C_{18}H_{32}N_6O_9S_4$ | 35.75 | 5.33 | 13.90 | 36.30 | 5.35 | 13.43 |
| XX | −N=C(CH₃)−SCH₃ | −C₆H₄−CH(CCl₃)−C₆H₄− | 174-176 | $C_{28}H_{33}Cl_3N_6O_8S_4$ | 41.20 | 4.07 | 10.30 | 41.51 | 4.21 | 10.23 |
| XXI | −N=C(dithiolane) | −(CH₂)₂− | 162-165 | $C_{18}H_{28}N_6O_8S_6$ | 33.32 | 4.32 | 12.95 | 33.19 | 4.23 | 12.33 |
| XXII | −N=C(dithiolane) | −C₆H₄−C(CH₃)₂−C₆H₄− | 122-124 | $C_{31}H_{38}N_6O_8S_6$ | 45.68 | 4.70 | 10.31 | 45.73 | 4.75 | 9.87 |

TABLE I-continued
PHYSICAL PROPERTIES $$R_2OC(O)-N(CH_3)-S-N(CH_3)-COXOC(O)-N(CH_3)-S-N(CH_3)-COR_2$$

| Example | R₂ | X | MP °C. | Molecular Formula | Calculated C | Calculated H | Calculated N | Found C | Found H | Found N |
|---|---|---|---|---|---|---|---|---|---|---|
| XXIII | 2,2-dimethyl-benzofuran-7-yl | -C₆H₄-C(CH₃)₂-C₆H₄- | oil | $C_{43}H_{48}N_4O_{10}S_2$ | 61.12 | 5.73 | 6.63 | 51.06 | 4.59 | 5.11 |
| | | | | (IR and NMR consistent with structure) | | | | | | |
| XXIV | 2,2-dimethyl-benzofuran-7-yl | —(CH₂)₆— | 104–118 | $C_{34}H_{46}N_4O_{10}S_2$ | 55.57 | 6.31 | 7.62 | 55.65 | 6.74 | 7.86 |
| XXV | 2,2-dimethyl-benzofuran-7-yl | —(CH₂)₂—O—(CH₂)₂— | oil | $C_{32}H_{42}N_4O_{11}S_2$ | 53.17 | 5.86 | 7.75 | 52.30 | 5.75 | 7.71 |
| XXVI | 2,2-dimethyl-benzofuran-7-yl | -C₆H₄-S-C₆H₄- | 80–90 | $C_{40}H_{42}N_4O_{10}S_3$ | 57.54 | 5.07 | 6.71 | 58.40 | 4.95 | 6.55 |
| XXVII | 2,2-dimethyl-benzofuran-7-yl | -C₆H₄-SO₂-C₆H₄- | 125–130 | $C_{40}H_{42}N_4O_{12}S_3$ | 55.41 | 4.88 | 6.46 | 55.19 | 4.77 | 6.37 |
| XXVIII | 2,2-dimethyl-benzofuran-7-yl | o-tolyl | 127–134 | $C_{34}H_{38}N_4O_{10}S_2 \cdot CH_2Cl_2$ | 51.79 | 4.97 | 6.90 | 52.45 | 4.95 | 6.97 |
| XXIX | 2,4,6-trimethylphenyl | -C₆H₄-C(=C(Cl)₂)-C₆H₄- | 160–163 | $C_{40}H_{42}Cl_2N_4O_8S_2$ | 57.07 | 5.03 | 6.66 | 56.94 | 5.00 | 6.62 |

Selected species of the new compounds were evaluated to determine their pesticidal activity against nematodes, mites and certain insects, including an aphid, a caterpillar, a beetle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The test concentrations in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (*Aphis fabae* Scop.) reared on potted dwarf nasturtium plants at 65°–70° F. and 50–70 percent relative humidity, constituted the test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°–70° F. and 50–70 percent, respectively. Aphids which fell onto the paper and were unable to remain standing after being uprighted were considered dead. Aphids remaining on the plants were observed closely for movement and those which were unable to move the length of the body upon stimulation by prodding, were considered dead. Percent mortality was recorded for various concentration levels.

Southern Armyworm Leaf Spray Test

Larvae of the southern armyworm (*Prodenia eridania*, (Cram.)), reared on Tendergreen bean plants at a temperature of 80±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis*, Muls.), reared on Tendergreen bean plants at a temperature of 80°±5° F. and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sparyed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F. for three days. Although the larvae could easily consume the leaf within 24 to 48 hours, no more food was added. Larvae which were unable to move the length of the body, even upon stimulation, were considered dead.

Fly Bait Test

Four to six day old adult house flies (*Musca domestica*, L.) reared according to the specifications of the Chemical Specialties Manufacturing Association (Blue Book, McNair-Dorland Co., N.Y. 1954; pages 243–244, 261) under controlled conditions of 80°±5° F. and 50±5 percent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a soufflé cup containing a one-inch square of an absorbent cotton pad. This bait cup was introduced and centered on the blotting paper under the food strainer prior to admitting the anesthetized flies. The caged flies were allowed to feed on the bait for twenty four hours, at a temperature of 80°±5° F. and the relative humidity of 50±5 percent. Flies which showed no sign of movement on prodding were considered dead.

Mite Foliage Spray Test

Adults and nymphal stages of the two-spotted mite (*Tetranychus urticae* Koch), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150–200 Mites, a sufficient number for testing, transferred from the excised leaves to the fresh plants in a period of twenty four hours. Following the twenty four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water solution containing acetone and emulsifier in the same concentrations as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding was considered living.

The results of these tests are set forth in Table I below. In these tests the pesticidal activity of the compounds against aphid, mite, Southern Armyworm, Bean Beetle and house fly was rated as follows:

A=excellent control
B=partial control
C=no control

POST-EMERGENT HERBICIDAL TEST

Experiments were also conducted to determine the phytotoxicity of representative compositions with respect to healthy fresh plants. Solutions of the compounds were prepared as described above to provide a concentration of 2500 parts per million of the test compound. The test plants were sprayed in accordance with the procedure described above for the Mite Foliage Spray Test so as to deliver approximately 100 milliliters of test solution to the leaves of each plant tested. The sprayed plants and controls were set aside for approximately one hour to allow the solutions to dry and were placed in the greenhouse. After ten days the plants were visually inspected to determine the extent of foliage injury. A rating of 1 indicates no perceptible injury; 5 indicates the plant was dead and ratings of 2, 3 and 4 indicate intermediate degree of injury based upon the number and extent to which leaves were injured.

The results of these experiments are summarized and set forth in Table II below.

TABLE II
BIOLOGICAL ACTIVITY
BIOLOGICAL ACTIVITY

| | Insecticidal and Miticidal Activity | | | | Phytotoxicity | | | | | A.O. |
|---|---|---|---|---|---|---|---|---|---|---|
| Ex. | Bean Aphid | Mite | Southern Armyworm | Mexican Bean Beetle | House-fly | Bean | Corn | Tomato | Cotton | Soybean | Rat mg/Kg |
| V | A | C | A | A | A | 1 | 1 | 1 | 1 | 1 | >640 |
| VI | A | C | A | A | A | 1 | 1 | 1 | 2 | 1 | — |
| VII | A | C | A | A | A | 1 | 1 | 1 | 1 | 1 | — |
| VIII | A | A | A | A | A | 1 | 1 | 1 | 3 | 1 | — |
| IX | A | A | A | A | A | 1 | 1 | 1 | 1 | 1 | <2 |
| X | A | C | A | A | A | 1 | 1 | 1 | 1 | 1 | — |
| XI | A | C | A | A | A | 1 | 1 | 1 | 1 | 1 | 453 |
| XII | C | C | A | A | A | 2 | 1 | 1 | 1 | 1 | — |
| XIII | A | C | A | A | A | 1 | 1 | 1 | 1 | 1 | 508 |
| XIV | A | C | A | A | A | 1 | 1 | 1 | 1 | 1 | >640 |
| XV | A | B | A | A | A | 1 | 1 | 1 | 2 | 1 | — |
| XVI | A | B | A | A | A | 1 | 1 | 1 | 3 | 1 | — |
| XVII | A | B | A | A | A | 1 | 1 | 1 | 1 | 1 | — |
| XVIII | C | B | C | C | C | 1 | 1 | 1 | 1 | 1 | — |
| XIX | A | C | A | A | A | 1 | 1 | 1 | 1 | 1 | — |
| XX | A | C | A | A | A | 1 | 1 | 1 | 1 | 1 | — |
| XXI | A | A | C | A | A | 1 | 1 | 1 | 2 | 1 | — |
| XXII | C | C | C | C | A | 1 | 1 | 1 | 1 | 2 | >640 |
| XXIII | B | B | A | A | A | 1 | 1 | 1 | 1 | 1 | — |
| XXIV | A | C | A | A | A | 1 | 1 | 1 | 1 | 1 | — |
| XXV | A | B | A | A | A | 1 | 1 | 1 | 1 | 1 | — |
| XVI | A | C | A | A | A | 1 | 1 | 1 | 1 | 1 | — |
| XXVII | B | C | A | A | A | 1 | 1 | 1 | 1 | 1 | — |
| XVIII | A | C | A | A | A | 2 | 1 | 1 | 1 | 1 | — |
| XXIX | B | B | B | B | C | 1 | 1 | 1 | 1 | 1 | — |

The results set forth in Table II clearly show the broad spectrum pesticidal activity of the compounds of this invention, as well as their reduced phytotoxicity and mammalian toxicity. It will be understood that the insect and mite species employed in the above tests are merely representative of a wide variety of pests that can be controlled through the use of the compounds of this invention.

The compounds contemplated in this invention may be applied as insecticides and miticides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spary so the rain does not re-emulsify the toxicant after it is applied to the plant and wash it off the plant. Nonionic, anionic, amphoteric, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pound of active toxicant per acre.

The pesticides contemplated herein prevent attack by insects, nematodes and mites upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultra-violet light, oxidation, or hydrolysis in the presence of moisture or, at least such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are compatible with substantially any other constituents of the spray schedule, and they may be used in the soil, upon the seeds, or the roots of plants without injuring either the seeds or roots of plants. They may also be used in combination with other pesticidally active compounds.

What is claimed is:

1. A compound of the formula:

wherein:

X is:
A. a substituted or unsubstituted divalent alkylene, alkenylene, alkynylene, monocyclic arylene, bicyclic arylene, biphenylene or a divalent alkylene chain which includes one oxygen, sulfur, sulfinyl, sulfonyl or nitrogen, wherein the permissible substituents are one or more alkyl, fluoro, nitro, chloro, or bromo groups.
B. a divalent organic radical of the formula:

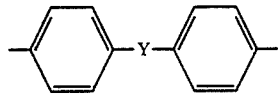

wherein:

Y is oxygen, sulfur, sulfinyl, sulfonyl, alkylene, haloalkylene, alkenylene, or haloalkenylene;

$R_1$ is alkyl having from one to four carbon atoms;

$R_2$ is:
A. dihydrobenzofuranyl, naphthyl, tetrahydronaphthyl, benzothienyl, indanyl, benzodioxalanyl, benzofuranyl, or benzodioxanyl, all of which may be either unsubstituted or substituted with one or more alkyl groups; or B. Phenyl, either unsubstituted or substituted with one or more halo, cyano, nitro, cycloalkyl, alkyl, 2-dioxalanyl, alkylthio, alkylsulfinyl, alkylsulfonyl, 2-dithiolanyl, alkylthioalkyl, alkylsulfonylalkyl, amino, alkylamino, dialkylamino, alkynyloxy, alkoxycarbonylamino, trihalomethyl, N,N-dialkylformamidino, alkoxy.

2. A compound according to claim 1 wherein $R_2$ is naphthyl or dihydrobenzofuranyl, either unsubstituted or substituted with one or more alkyl groups or phenyl, either unsubstituted or substituted with one or more alkyl, alkylthio, dialkylamino, alkynyloxy or alkoxy.

3. An insecticidal, and nematocidal composition comprising an acceptable carrier and as the active toxicant an insecticidally, miticidally or nematocidally effective amount of a compound according to claim 2.

4. A method of controlling insects, mites and nematodes which comprises applying to them an insecticidally miticidally or nematocidally effective amount of a compound according to claim 2.

5. An insecticidal, and nematocidal composition comprising an acceptable carrier and as the active toxicant an insecticidally, miticidally or nematocidally effective amount of compound according to claim 1.

6. A method of controlling insects, mites and nematodes which comprises subjecting them to an insecticidally miticidally or nematocidally effective amount of a compound according to claim 1.

7. 1,2-Bis-[[N-methyl-N-[N'-7-(2,3-dihydro-2,2-dimethylbenzofuranyloxycarbonyl)-N'-methylaminosulfenyl] carbamoyloxy]] ethane.

8. An insecticidal, and nematocidal composition comprising an acceptable carrier and as the active toxicant an insecticidally, miticidally or nematocidally effective amount of compound according to claim 7.

9. A method of controlling insects, mites and nematodes which comprises applying to them an insecticidally miticidally or nematocidally effective amount of a compound according to claim 7.

* * * * *